(12) United States Patent
Yamada et al.

(10) Patent No.: US 8,771,535 B2
(45) Date of Patent: Jul. 8, 2014

(54) SAMPLE CONTAMINATION METHOD

(75) Inventors: Yuji Yamada, Yokohama (JP); Makiko Katano, Yokohama (JP); Ayako Mizuno, Yokohama (JP); Eri Uemura, Yokohama (JP); Asuka Uchinuno, Yokohama (JP); Chikashi Takeuchi, Yokohama (JP)

(73) Assignee: Kabushiki Kaisha Toshiba, Tokyo (JP)

(*) Notice: Subject to any disclaimer, the term of this patent is extended or adjusted under 35 U.S.C. 154(b) by 132 days.

(21) Appl. No.: 13/188,719

(22) Filed: Jul. 22, 2011

(65) Prior Publication Data
US 2012/0149199 A1 Jun. 14, 2012

(30) Foreign Application Priority Data
Dec. 10, 2010 (JP) .............. P2010-275338

(51) Int. Cl.
*H01L 21/66* (2006.01)
*G01N 1/28* (2006.01)

(52) U.S. Cl.
USPC ........... 216/59; 216/84; 427/96.1; 427/96.7; 427/123; 427/421.1; 438/14; 438/758; 438/909; 134/902

(58) Field of Classification Search
None
See application file for complete search history.

(56) References Cited

U.S. PATENT DOCUMENTS

| | | | | |
|---|---|---|---|---|
| 6,323,136 B1 * | 11/2001 | Shiramizu | ............. | 438/745 |
| 6,969,621 B1 * | 11/2005 | Gatov | ............. | 438/14 |
| 7,811,836 B2 * | 10/2010 | Lee et al. | ............. | 438/14 |
| 2002/0142474 A1* | 10/2002 | LaGraff et al. | ............. | 436/73 |
| 2007/0044713 A1* | 3/2007 | Yasui et al. | ............. | 118/300 |
| 2010/0300221 A1* | 12/2010 | Lee et al. | ............. | 73/866 |

FOREIGN PATENT DOCUMENTS

| | | | |
|---|---|---|---|
| JP | 4-27398 | | 1/1992 |
| JP | 11-142389 A | * | 5/1999 |
| JP | 11-211628 | | 8/1999 |
| JP | 2002-350301 | | 12/2002 |

* cited by examiner

*Primary Examiner* — Anita Alanko
(74) *Attorney, Agent, or Firm* — Finnegan, Henderson, Farabow, Garrett & Dunner, L.L.P.

(57) ABSTRACT

A sample contamination method according to an embodiment includes spraying a chemical solution containing contaminants into a casing, carrying a semiconductor substrate into the casing filled with the chemical solution by the spraying, leaving the semiconductor substrate in the casing filled with the chemical solution for a predetermined time, and carrying the semiconductor substrate out of the casing after the predetermined time passes.

13 Claims, 4 Drawing Sheets

SAMPLE CONTAMINATION METHOD

CROSS-REFERENCE TO RELATED APPLICATION

This application is based upon and claims the benefit of priority from the prior Japanese Patent Application No. 2010-275338, filed on Dec. 10, 2010; the entire contents of which are incorporated herein by reference.

FIELD

Embodiments described herein relate generally to a sample contamination method for evaluating the influence of contaminants on a semiconductor device.

BACKGROUND

Contaminants (for example, metal and organic matters) adversely affect characteristics (electric characteristics in particular) of a semiconductor device. In the manufacturing process of the semiconductor device, various materials and apparatuses are used, where there are problems of contamination of the semiconductor device by these materials and cross-contamination among the apparatuses. In an evaluation test of the semiconductor device, it is inevitable to contaminate the semiconductor device with an arbitrary concentration, and evaluate how the characteristics of the semiconductor device change. For example, as a method for contaminating the semiconductor device with an arbitrary concentration, there has been proposed a method to spray a chemical solution with an arbitrary concentration via a spray nozzle onto the semiconductor device while rotating a substrate on which the semiconductor device is formed.

DETAILED DESCRIPTION

A sample contamination method according to an embodiment includes spraying a chemical solution containing contaminants into a casing, carrying a semiconductor substrate into the casing filled with the chemical solution by the spraying, leaving the semiconductor substrate in the casing filled with the chemical solution for a predetermined time, and carrying the semiconductor substrate out of the casing after the predetermined time passes.

Hereinafter, an embodiment will be described in detail with reference to the drawings.

Embodiment

Figure 1:
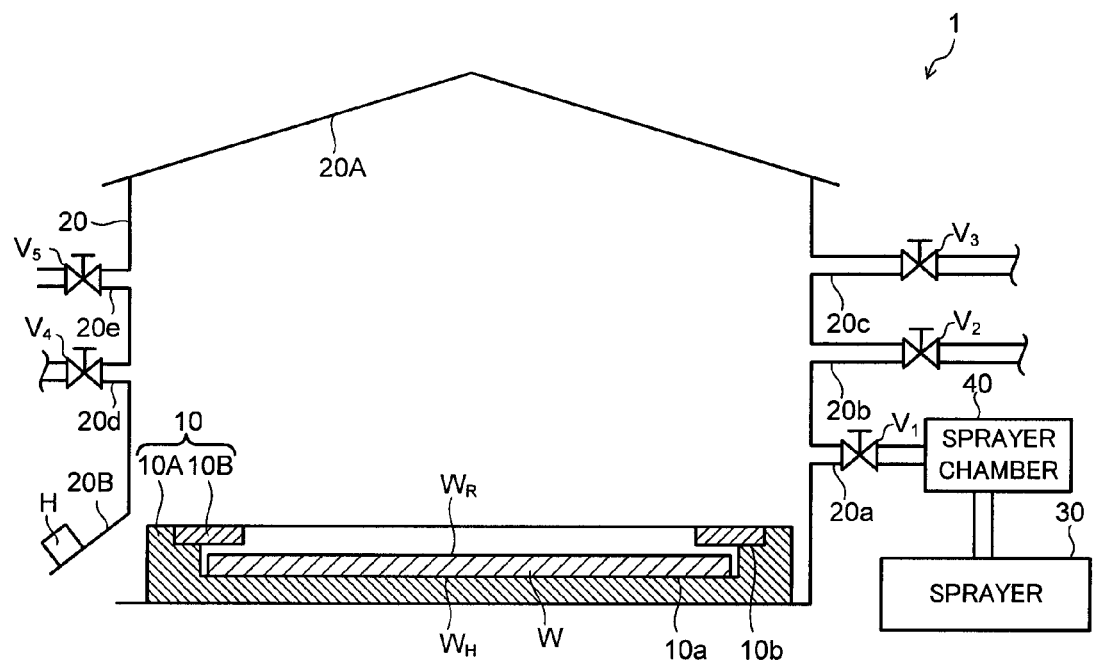
FIG. 1 is a structural cross-sectional diagram of a sample contamination apparatus according to an embodiment.

FIG. 1 is a structural cross-sectional diagram of a sample contamination apparatus 1 according to an embodiment. As illustrated in FIG. 1, the sample contamination apparatus 1 has a substrate container 10, a spray container (casing) 20, a sprayer 30, and a spray chamber 40. In this embodiment, although the case where a chemical solution containing contaminants is adhered to a rear face $W_R$ of the substrate W will be described, contamination with the chemical solution is not limited to the rear face $W_R$. For example, a front face $W_H$ on which the semiconductor device is formed may be contaminated. The sample contamination apparatus 1 can pollute a semiconductor substrate W (hereinafter referred to as a substrate W) which is a contamination target, inspective of the state of the surface (kind of film, shape and pattern) of the substrate W.

Figure 2:
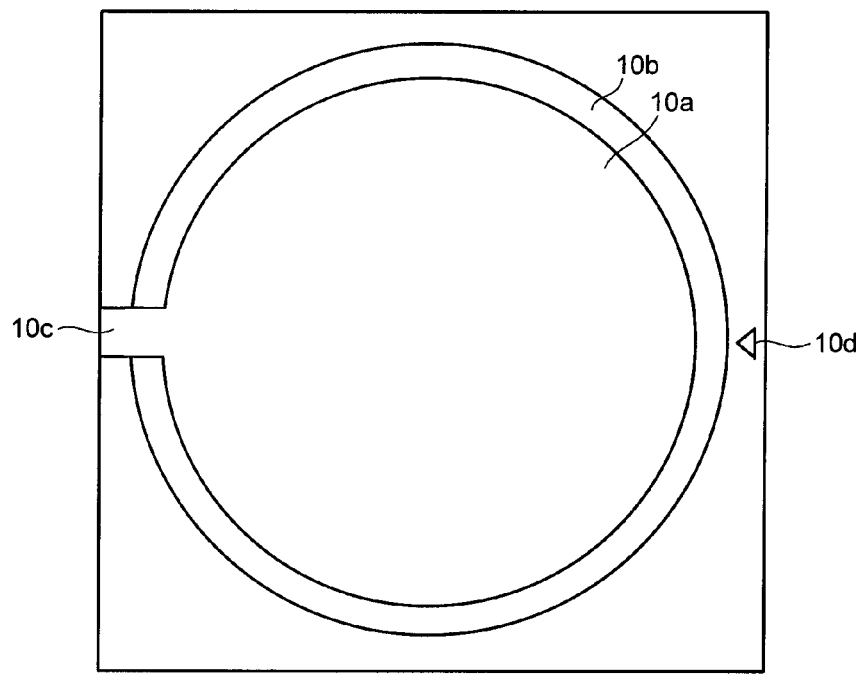
FIG. 2 is a top view of a substrate container.

The substrate container 10 has a main body 10A to house the substrate W which is a contamination target, and a cover ring 10B to cover a peripheral portion of the substrate W on the main body 10A. FIG. 2 is a top view of the substrate container 10.

FIG. 2 illustrates a state that the cover ring 10B is removed. In the main body 10A, there are formed a substrate mounting surface 10a on which the substrate W is mounted, a cover ring mounting surface 10b on which the cover ring 10B is mounted, a cutout portion 10c allowing escaping of an instrument such as a forceps used for handling the substrate, and a mark 10d indicating the position of a notch. The substrate W is housed in the main body 10A in a manner of being mounted on the substrate mounting surface 10a of the main body 10A. In this embodiment, the substrate W is mounted on the substrate mounting surface 10a of the main body 10A with its rear face $W_R$ being the upper side.

The cover ring 10B prevents contamination of a metal ring attached onto an outer peripheral portion of the substrate W when the rear face of the substrate W is ground. The cover ring 10B has a size which hides the metal ring (in this embodiment, the rear face of the substrate W is not to be ground, and thus an illustration of the metal ring is omitted). The cover ring 10B prevents adherence of liquid drops to the metal ring. The cover ring 10B is removable from the main body 10A. The cover ring 10B is removed when the metal ring is not used. The metal ring can be replaced by a ring made of resin other than metal.

The spray container 20 has a sealable structure for filling the chemical solution containing contaminants (for example, metal and organic matters) sprayed from the sprayer 30, which will be described later. The spray container 20 is made of the material that has corrosion resistance to the chemical solution (for instance, polyethylene) in order to prevent the corrosion thereof by acid and alkali contained in HF (hydrogen fluoride) and the atomization drug solution described later.

The spray container 20 is provided with an openable and closable lid (door) 20B. In a state that the lid 20B is opened, the substrate container 10 housing the substrate W is carried in and out of the spray container 20. Other than when the substrate container 10 is carried in or out, the lid 20B is closed to maintain airtightness of the spray container 20. To open or close the lid 20B, a handle H is used.

The spray container 20 is provided with conduits 20a, 20b, 20c, an exhaust pipe 20d, and a release pipe 20e. The conduit 20a has a valve $V_1$. By opening the valve $V_1$, the chemical solution containing contaminants sprayed from the sprayer 30, which will be described later, is introduced into the spray container 20. By a typical method, the position of the conduit 20a is often provided at an upper part of the spray container 20. However, in this embodiment, the substrate W is carried into the spray container 20 in a state that the chemical solution is filled therein, and thus there is an advantage that the position of the conduit 20a is not limited.

The conduit 20b has a valve $V_2$. By opening the valve $V_2$ nitrogen gas ($N_2$) for purging or clean dry air (CDA) is introduced into the spray container 20. The conduit 20c has a valve $V_3$. By opening the valve $V_3$, mist of HF (hydrogen fluoride) is introduced into the spray container 20.

When the rear face $W_R$ of the substrate W is exposed to HF, a silicon dioxide ($SiO_2$) formed on the rear face $W_R$ of the substrate W is removed, and the rear face $W_R$ of the substrate W changes from hydrophilic to hydrophobic. Mist of HF (hydrogen fluoride) introduced into the spray container 20 hardly be made contact with the front surface $W_H$ of the substrate W. In addition, the semiconductor device formed on the front face $W_H$ of the substrate W is normally protected by a passivation film (protection film) such as a silicon nitride film ($Si_3N_4$ film), a polyimide film, a BPSG (Boro-Phospho-Silicate-Glass), or the like, and thus is barely affected by HF.

The exhaust pipe 20d is connected to a not-illustrated pump. The exhaust pipe 20d has a valve $V_4$. By opening the valve $V_4$, the chemical solution containing contaminants introduced into the spray container 20 and HF are exhausted to the outside of the spray container 20. The release pipe 20e has a valve $V_5$. By opening the valve $V_5$, the inside of the spray container 20 is released to open air.

By changing from hydrophilic to hydrophobic by removing a silicon oxide film on the rear face $W_R$ of the substrate W, it is possible to prevent aggregation of liquid drops adhering to the rear face $W_R$ of the substrate W. As a consequence, finer liquid drops can be adhered to the rear face $W_R$ of the substrate W. Accordingly, liquid drops with substantially the same diameter are uniformly distributed on the substrate W, and thus the concentration of contaminants on the rear face $W_R$ of the substrate W becomes uniform. The present inventors have confirmed that adjacent liquid drops aggregate to be a large liquid drop when the rear face $W_R$ of the substrate W is hydrophilic (when a silicon oxide film exists on the rear face $W_R$), and that liquid drops do not aggregate together but adhere uniformly to the rear face $W_R$ of the substrate W when the rear face $W_R$ of the substrate W is hydrophobic (when the silicon (Si) surface is exposed by removing the silicon oxide film on the rear face $W_R$).

A ceiling 20A is attached to incline at a predetermined angle from a horizontal plane. By inclining the ceiling 20A, even when liquid drops adhering to the ceiling 20A aggregate to be a large liquid drop, the liquid drops flow down to a wall face in the spray container 20 along this inclination. Accordingly, it is possible to prevent the liquid drops which became large from dripping on the substrate W. To the ceiling 20A of the spray container 20, preferably, a surface treatment (for example, treatment to prevent condensation or treatment to increase its water absorbing property) is provided for preventing liquid drops adhering to the ceiling 20A from aggregating and dripping onto the substrate W.

Figure 3A:
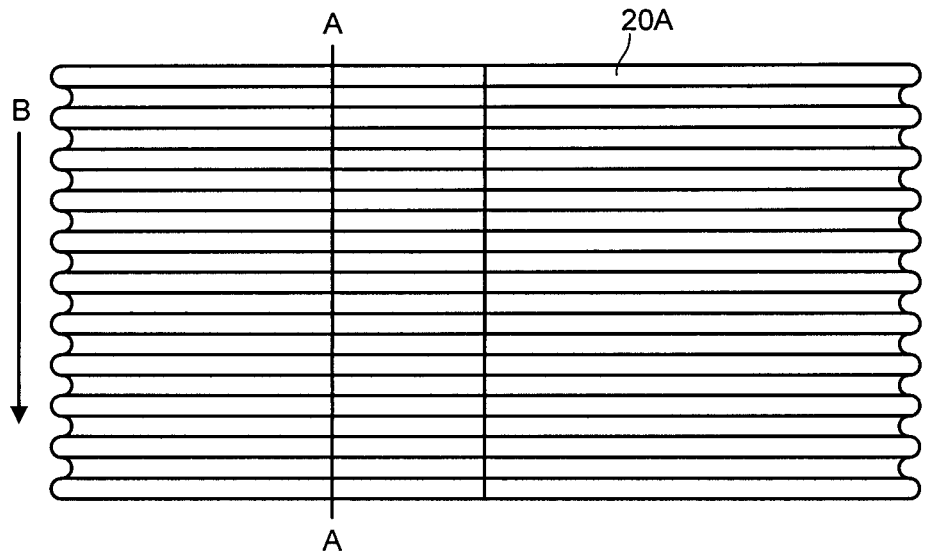
FIGS. 3A and 3B are structural views of a ceiling of a spray container.
Figure 3B:
Figure 4:
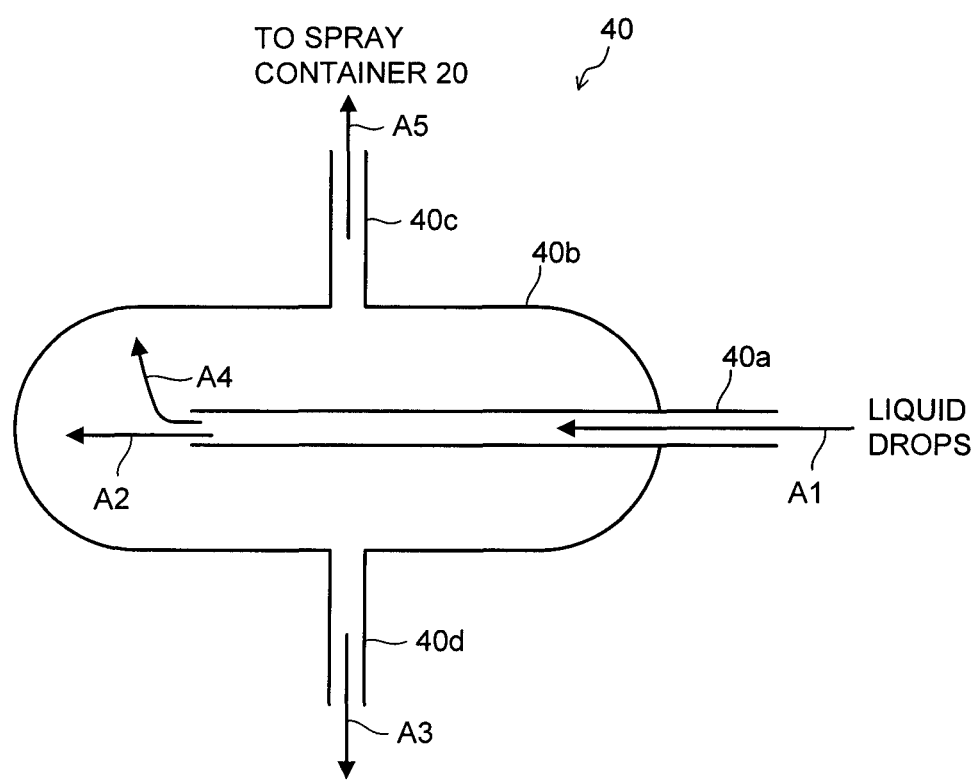
FIG. 4 is a structural diagram of a spray chamber.

FIGS. 3A and 3B are structural views of the ceiling 20A of the spray container 20. FIG. 3A is a top view of the ceiling 20A. FIG. 3B is a cross-sectional structural view taken along a line A-A of FIG. 3A. The ceiling 20A is formed of two corrugated plates as illustrated in FIGS. 3A and 3B, and is disposed so that the direction in which waves of the corrugated plates are formed (the direction of arrow B of FIG. 3A) is orthogonal to the inclining direction of the ceiling 20A. By such a structure, dripping of liquid drops onto the substrate W can be prevented more effectively. The ceiling 20A is removable, and thus maintainability (for example, cleaning the inside of the spray container 20) improves.

The sprayer 30 is a nebulizer which sprays the chemical solution containing contaminants in the form of small liquid drops. As the sprayer 30, preferably, there is used a glass concentric nebulizer (for example, a concentric nebulizer made by MEINHARD) which sprays nitrogen gas ($N_2$) or the like at high speed to a chemical solution pushed out of the tip of a liquid delivery pipe to turn it into small liquid drops, or a ultrasonic nebulizer (for example, an ultrasonic nebulizer made by Epolead) which turns a chemical solution into small liquid drops by ultrasonic waves. This is because when a heated nebulizer which turns a chemical solution into small liquid drops by heating is used, the concentration of contaminants in the chemical solution and the concentration of contaminants in the chemical solution which became liquid drops by heating will be different values due to a difference in mist pressure.

The spray chamber 40 intervenes between the spray container 20 and the sprayer 30, allows passing of ones with a particle diameter smaller than a predetermined value among liquid drops delivered from the sprayer 30, but does not allow passing of ones with a particle diameter equal to or larger than the predetermined value. By allowing the liquid drops delivered from the sprayer 30 to pass through the spray chamber 40, particle diameters of the chemical solution to be introduced into the spray container 20 can be uniformed. As a consequence, the uniformity of particle diameters of the chemical solution to be adhered to the rear face $W_R$ of the substrate W can be improved. Accordingly, the concentration of contaminants on the rear face $W_R$ of the substrate W can be uniformed effectively.

FIG. 4 is a structural diagram of the spray chamber 40. The spray chamber 40 has a conduit 40*a* which introduces liquid drops of the chemical solution from the sprayer 30, a main body part 40*b* which separates ones with a particle diameter equal to or larger than a predetermined value (for example, 40 μm) and ones with a particle diameter smaller than the predetermined value among the liquid drops introduced by the conduit 40*a*, a discharge pipe 40*c* which discharges the liquid drops with a particle diameter smaller than the predetermined value, which are separated by the main body part, to the spray container, and a drain pipe 40*d* which discharges the liquid drops with a particle diameter equal to or larger than the predetermined value.

Next, the operation principle of the spray chamber 40 will be described. Liquid drops introduced via one end of the conduit 40*a* proceed through the conduit 40*a* and reach the other end of the conduit 40*a* (see arrow A1 of FIG. 4). At this time, the liquid drops with a particle diameter equal to or larger than the predetermined value are less affected by air resistance due to their large mass. Accordingly, the liquid drops with a particle diameter equal to or larger than the predetermined value collide with an inner wall of the main body part 40*b* (see arrow A2 of FIG. 4), aggregate to be a certain size or larger, and thereafter travels on the inner wall of the main body part 40*b* to be discharged from the main body part 40*b* via the drain pipe 40*d* (see arrow A3 of FIG. 4).

On the other hand, the liquid drops with a particle diameter smaller than the predetermined value are more affected by air resistance due to their small mass. Accordingly, they are guided to the discharge pipe 40*c* without colliding with the inner wall of the main body part 40*b* (see arrow A4 of FIG. 4), and are discharged via the discharge pipe 40*c* (see arrow A5 of FIG. 4). The discharged liquid drops of the chemical solution are introduced into the spray container 20. By adjusting the introduction rate of liquid drops into the conduit 40*a*, liquid drops with a desired particle diameter can be removed.

First, a normal operation of the sample contamination apparatus 1 will be described. In the description below, it is assumed that all the valves $V_1$ to $V_5$ are closed when the operation is started.

The substrate W as the target of contamination is mounted on the substrate mounting surface 10*a* of the main body 10A with the rear face $W_R$ being the upper side, before carried into the spray container 20. When the rear face of the substrate W is ground and the metal ring is attached to the outer peripheral portion of the substrate W, the cover ring 10B is mounted on the cover ring mounting surface 10b. Next, the chemical solution containing contaminants adjusted to a predetermined concentration is set in the sprayer 30, and the sprayer 30 is activated. The valve $V_1$ of the conduit 20a and the valve $V_5$ of the release pipe 20e are opened in advance.

When the sprayer 30 is activated, small liquid drops (with a diameter of about 30 μm) of the chemical solution are produced and introduced into the spray chamber 40. Among the liquid drops delivered from the sprayer 30, ones with a particle diameter smaller than the predetermined value pass through the spray chamber 40, and ones with a particle diameter equal to or larger than the predetermined value do not pass through. In the spray chamber 40, ones with a particle diameter equal to or larger than the predetermined value are removed, and ones with a particle diameter smaller than the predetermined value are introduced into the spray container 20 via the conduit 20a.

When a predetermined time (generally, about one minute) passes from activation of the sprayer 30, the spray container 20 is filled with small liquid drops of the chemical solution. Whether the spray container 20 is filled with liquid drops of the chemical solution or not can be checked by whether liquid drops of the chemical solution come out of the release pipe 20e. When the spray container 20 is filled with small liquid drops of the chemical solution, the valve $V_1$ is closed and the sprayer 30 is stopped. The substrate W may be mounted on the substrate mounting surface 10a of the main body 10A while the sprayer 30 is activated and the spray container 20 is filled with small liquid drops of the chemical solution.

After the spray container 20 is filled with small liquid drops of the chemical solution, leaving at rest for a predetermined time (generally, about thirty seconds) until comparatively bigger liquid drops in the spray container 20 falls. Then, the lid 20B of the spray container 20 is opened. The substrate container 10 housing the substrate W is carried quietly into the spray container 20. After the substrate container 10 is carried into the spray container 20, the lid 20B of the spray container 20 is closed. If the droplet distribution in the spray container 20 is not stable when the substrate container 10 is carried into the spray container 20, the droplet distribution in the spray container 20 can be improved by opening the valve $V_1$ and starting the sprayer 30 for a predetermined time (generally, about five seconds).

After a predetermined time (generally, about one minute) passes, the lid 20B of the spray container 20 is opened, and the substrate container 10 housing the substrate W is taken out of the spray container 20. The substrate W is taken out of the substrate container 10 and a necessary test is performed.

Next, an operation of the sample contamination apparatus 1 when HF is used will be described. In the following description, it is assumed that all the valves $V_1$ to $V_5$ are closed when the operation is started.

The substrate W as the target of contamination is mounted on the substrate mounting surface 10a of the main body 10A with the rear face $W_R$ being the upper side. The lid 20B of the spray container 20 is opened, and the substrate container 10 housing the substrate W is carried into the spray container 20. After the substrate container 10 is carried into the spray container 20, the lid 20B of the spray container 20 is closed. At this time, the lid 20B is closed tightly to maintain airtightness of the spray container 20.

Next, the valve $V_3$ of the conduit 20c is opened, and HF mist is introduced into the spray container 20. After the HF mist is introduced into the spray container 20, the substrate is left until the oxide film formed on the rear face $W_R$ of the substrate W is removed. After the HF mist is introduced into the spray container 20, the valve $V_3$ of the conduit 20c is closed.

The valve $V_4$ of the exhaust pipe 20e is opened to exhaust the HF mist and the product of the HF mist and silicon fluoride in the spray container 20. The valve $V_2$ of the conduit 20b is opened to introduce nitrogen gas into the spray container 20. After the inside of the spray container 20 is replaced with the nitrogen gas, the valve $V_4$ of the exhaust pipe 20e and the valve $V_2$ of the conduit 20b are closed.

The lid 20B of the spray container 20 is opened, and the substrate container 10 housing the substrate W is carried out of the spray container 20 once. The operation procedure after this is the same as the normal operation of the sample contamination apparatus 1, and thus the duplicated description is omitted.

As described above, the sample contamination apparatus 1 according to the embodiment has the sprayer 30 spraying the chemical solution containing contaminants into the spray container 20, and the substrate container 10 housing the substrate W is carried into the spray container 20 in a state that the spray container 20 is filled with the chemical solution. Accordingly, the substrate W as the target of contamination can be contaminated with high uniformity in a short time.

Since the apparatus has the spray chamber 40 which removes liquid drops with a particle diameter equal to or larger than a predetermined value in the chemical solution sprayed from the sprayer 30, the particle diameters of liquid drops of the chemical solution introduced into the spray container 20 can be uniformed, and contamination of the substrate W as the contamination target can be uniformed further. Rotating the substrate W is not necessary, and thus it is possible to contaminate a thin substrate W after being ground. It is not necessary to adjust the mounting position, angle, and the like of a spray nozzle for spraying the chemical solution, and thus convenience for the user improves.

Since the valve $V_1$ is closed after the spray container 20 is filled with small liquid drops of the chemical solution, when the substrate container 10 housing the substrate W is carried into the spray container 20, there is almost no concern of dripping of liquid drops with a large particle diameter onto the rear face $W_R$ of the substrate W. The sprayer 30 is also stopped, and thus the chemical solution would not be wasted.

Next, evaluation results of a sample (example) prepared using the sample contamination apparatus 1 according to the embodiment and a sample (comparative example) prepared using a conventional technique will be described.

Example

The contaminated sample of the example was prepared by spraying a dilute nitric acid in which copper (Cu) is dissolved by the sprayer 30 (concentric nebulizer made by MEINHARD) into the spray container 20 of the sample contamination apparatus 1 described with FIG. 1, leaving the spray container for a certain time, and thereafter housing in the spray container 20 the substrate container 10 in which a substrate W (Bare-Si substrate) with a diameter of 300 mm is mounted and leaving the substrate container for one minute. The particle diameter of the sprayed dilute nitric acid is about 30 μm. Further, in this example, the spray chamber 40 was not used.

Comparative Example

The contaminated sample of the comparative example was prepared by spraying a dilute nitric acid in which copper (Cu)

is dissolved using a spray onto the substrate W (Bare-Si substrate) with a diameter of 300 mm. The concentration of dissolved copper in the dilute nitric acid is the same as in the example.

Figure 5A:
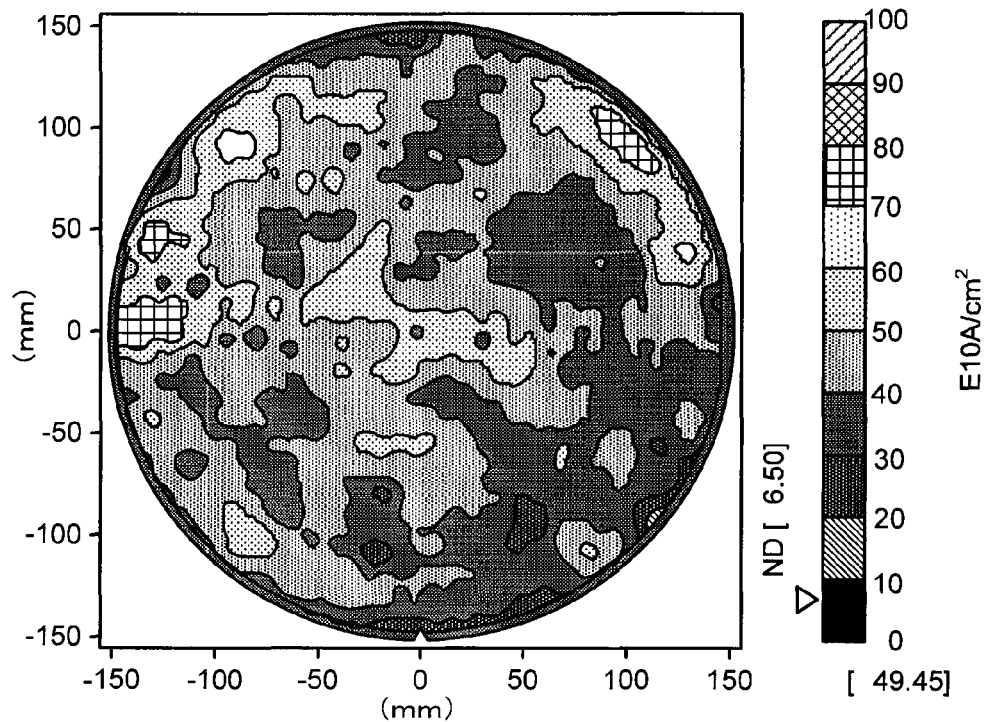
FIGS. 5A and 5B are diagrams illustrating evaluation results of examples and comparative examples.
Figure 5B:
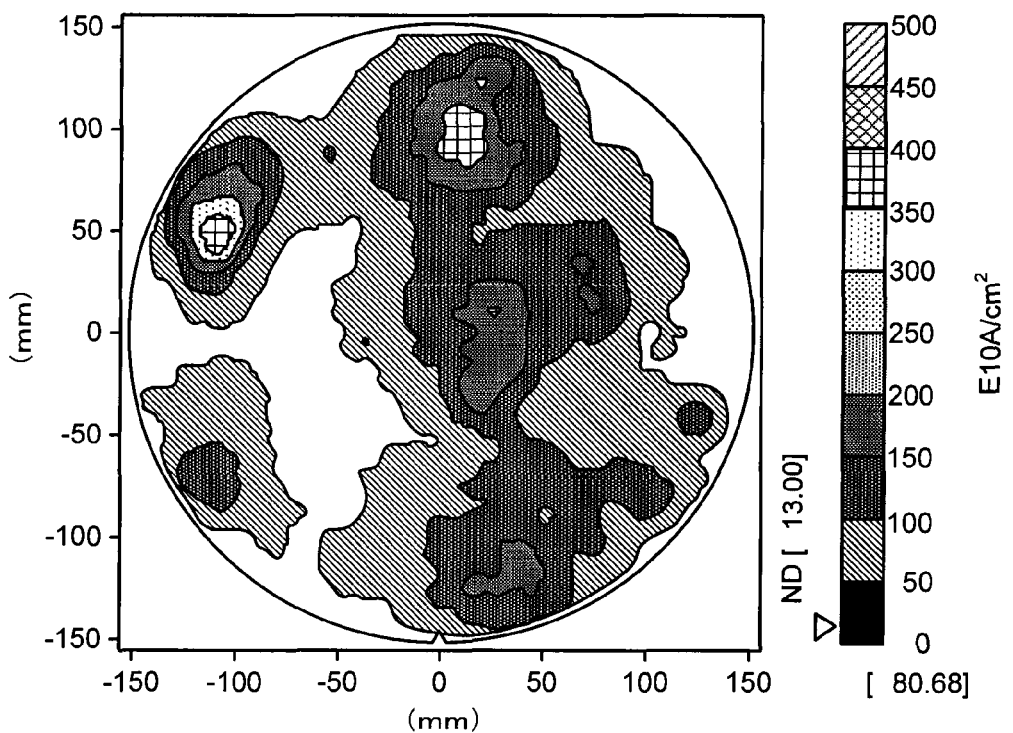

FIGS. 5A and 5B are diagrams illustrating measurement results (concentration distribution of Cu) of the example and the comparative example. FIG. 5A is a diagram illustrating evaluation results of the example. FIG. 5B is a diagram illustrating evaluation results of the comparative example. For measurement of the contaminated samples, a total reflection X-ray fluorescence spectrometer (TXRF-V300 made by Rigaku) was used. In addition, unpatterned (white) areas on the sample (wafer W) of FIG. 5B denote an area where the Cu concentration is equal to or less than the detection limit ($1.3 \times 10^{11}$ atoms/cm$^2$).

As illustrated in FIGS. 5A and 5B, the concentration distribution of Cu adhering to the substrate W in the sample of the example (see FIG. 5A) is in the range of $2 \times 10^{11}$ (atoms/cm$^2$) to $8 \times 10^{11}$ (atoms/cm$^2$). The concentration distribution of Cu adhering to the substrate W in the sample of the comparative example (see FIG. 5B) is in the range of $1 \times 10^{11}$ (atoms/cm$^2$) to $4 \times 10^{12}$ (atoms/cm$^2$). It can be seen that the sample of the example clearly excels in uniformity compared to the sample of the comparative example. Accordingly, it can be seen that a sample contaminated with high uniformity can be prepared by using the sample contamination apparatus 1 according to this embodiment.

Next, the relation between an adhering amount (contamination concentration) of Cu to samples (substrates W) and exposure times will be described. Table 1 illustrates the relation between an adhering amount (contamination concentration) of Cu to the samples (substrates W) and the exposure times. The samples in Table 1 were prepared by filling a dilute nitric acid in which copper (Cu) is dissolved by the sprayer 30 (concentric nebulizer made by MEINHARD) in the spray container 20 of the sample contamination apparatus 1 described with FIG. 1, and thereafter housing in the spray container 20 the substrate container 10 in which the substrate W with a diameter of 300 mm is mounted, and leaving the substrate container for a predetermined time for each sample (1 minute, 2 minutes 30 seconds, 5 minutes, or 10 minutes). The spray chamber 40 was not used.

TABLE 1

| Sample | Exposure time | Contamination amount (atoms/cm$^2$) | Standard deviation (%) |
|---|---|---|---|
| A | 1 min | 5.26E+12 | 21.8% |
| B | 2 min 30 sec | 5.63E+12 | 25.4% |
| C | 5 min | 5.18E+12 | 29.4% |
| D | 10 min | 5.10E+12 | 36.8% |

From the results of Table 1, it can be seen that the contamination amounts of Cu of the samples A to D barely change even when the exposure time is changed from 1 minute to 10 minutes. On the other hand, the in-plane standard deviation representing in-plane uniformity of the samples A to D worsens as the exposure time becomes longer, and is higher than 30% when the exposure time is 10 minutes. Thus, when a contamination sample is prepared using the sample contamination apparatus 1 according to the embodiment, the exposure time is preferably in the range of 1 minute to 5 minutes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A sample contamination method, comprising:
   introducing a chemical solution containing metal contaminants in the form of chemical liquid drops into a casing;
   carrying a semiconductor substrate in a state of lying on a substrate container into the casing filled with the chemical liquid drops;
   leaving the semiconductor substrate in the casing filled with the chemical liquid drops for a first predetermined time; and
   carrying the semiconductor substrate out of the casing after the first predetermined time passes.

2. The method according to claim 1, further comprising:
   between the steps of introducing the chemical solution into the casing and carrying the semiconductor substrate into the casing filled with the chemical liquid drops stopping the introducing of the chemical solution.

3. The method according to claim 1, further comprising:
   before the step of introducing the chemical solution into the casing, carrying the semiconductor substrate into the casing, introducing hydrogen fluoride (HF) mist into the casing to remove an oxide film formed on the semiconductor substrate, and changing a surface of the semiconductor substrate from hydrophilic to hydrophobic.

4. The method according to claim 1, further comprising:
   before the step of introducing the chemical solution into the casing, removing, from the chemical solution, liquid drops with a particle diameter equal to or larger than a predetermined value in a spray chamber.

5. The method according to claim 1, further comprising:
   before the step of carrying the semiconductor substrate into the casing filled with the chemical liquid drops, leaving at rest for a second predetermined time.

6. The method according to claim 1, further comprising:
   spraying the chemical solution into the casing for a third predetermined time when carrying the semiconductor substrate into the casing filled with the chemical liquid drops.

7. The method according to claim 1,
   wherein the contaminants further contain organic matters.

8. The method according to claim 1,
   wherein the first predetermined time is one minute.

9. The method according to claim 4,
   wherein the predetermined value is 40 μm.

10. The method according to claim 5,
    wherein the second predetermined time is 30 seconds.

11. The method according to claim 1, further comprising:
    covering a part of the substrate before carrying the semiconductor substrate into the casing.

12. The method according to claim 1,
    wherein the chemical solution is introduced from the side of the casing.

13. The method according to claim 1,
    wherein the chemical solution is introduced in the form of liquid drops by a nebulizer.

* * * * *